United States Patent [19]

Keefer et al.

[11] Patent Number: 5,039,705

[45] Date of Patent: Aug. 13, 1991

[54] ANTI-HYPERTENSIVE COMPOSITIONS OF SECONDARY AMINE-NITRIC OXIDE ADDUCTS AND USE THEREOF

[75] Inventors: Larry K. Keefer, Bethesda; David A. Wink, Frederick; Tambra M. Dunams, Frederick; Joseph A. Hrabie, Frederick, all of Md.

[73] Assignee: The United States of America as represented by the Department of Health and Human Services, Washington, D.C.

[21] Appl. No.: 409,552

[22] Filed: Sep. 15, 1989

[51] Int. Cl.$^5$ .................. A61K 31/13; A61K 31/20; A61K 31/195; A61K 31/655

[52] U.S. Cl. ................ 514/611; 514/149; 514/558; 514/563; 514/564; 514/579; 514/610; 514/645

[58] Field of Search .............. 514/611, 149, 558, 563, 514/564, 610, 645, 579

[56] References Cited

U.S. PATENT DOCUMENTS 3,153,094  10/1984  Reilly ................................. 260/576

OTHER PUBLICATIONS

Palmer, Nature 327, 524–526, 1987.
Kruszyna et al. Toxicol. and Applied Pharmacol. 91, 429–438, 1987.
Ignarro, The FASEB Journal 3, 31–36, 1989.
Ignarro et al., J. Pharmacol. & Exper. Therapeutics 218(2), 739–749, 1981.
Drago, "Free Radicals in Inorganic Chemistry", No. 36, Advances in Chemistry Series, Amer. Chem. Soc., Wash. DC, 1962, pp. 143–149.
Drago et al., J. Amer. Chem. Soc. 83, 1819–1822, 1961.
Deluca et al., "Pharmaceutics and Pharmacy Practice" J.B. Lippincott Co., Philadelphia, 1982, 238–250.
Trissel, ASHP, "Handbook on Injectable Drugs" 4th ed; 622–630, 1986.

Primary Examiner—Allen J. Robinson
Attorney, Agent, or Firm—John Bailey; Robert Benson

[57] ABSTRACT

This invention concerns anti-hypertensive compositions and a method of lowering blood pressure in mammals. The active component of the compositions is a compound of the formula:

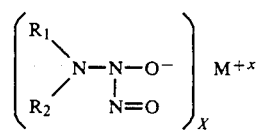

wherein $R_1$ and $R_2$ are independently chosen from straight chain and branched chain $C_1$–$C_{12}$ alkyl groups and benzyl, with the proviso that no branch occur on the alpha carbon atom of the alkyl groups; or $R_1$ and $R_2$ together with the nitrogen atom they are bonded to form a pyrrolidino, piperidino, piperazino or morpholino group, $M^+$ is a pharmaceutically acceptable cation, wherein X is the valence of the cation.

14 Claims, No Drawings

ANTI-HYPERTENSIVE COMPOSITIONS OF SECONDARY AMINE-NITRIC OXIDE ADDUCTS AND USE THEREOF

INTRODUCTION

This invention concerns novel pharmaceutical compositions and a method of treating hypertension. Related compositions and methods are described in U.S. Pat. application SN No. 07/316,958, filed Feb. 28, 1989, now U.S. Pat. No. 4,954,526, and in SN 07/423,279, filed on Nov. 18, 1989.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann.Rev.Pharmacol.Toxicol. 24, 175-197, 1984.) Recently, Palmer et al., have shown that EDRF is identical to the simple molecule, nitric oxide, NO. (Nature 317, 524-526, 1987.) It has been hypothesized for years that many nitrovasodilators that mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox.& Appl. Pharmacol., 91, 429-438, 1987; Ignarro, FASEB J. 3, 31-36, 1989 and Ignarro et al., J. Pharmacol. Exper. Theraputics 218(3), 739-749, 1981.) It has now been discovered that a class of compounds of the structure:

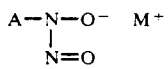

wherein A is a secondary amino group, are potent anti-hypertensives and thus are useful for treating cardiovascular disorders in which lowering the blood pressure has a beneficial result. It is believed that these compounds function by releasing NO in the blood after injection; however the invention should not be limited by this hypothesis. While these compounds are, for the most part, known, there is no suggestion in the prior art that they are anti-hypertensive, indeed, there is no suggestion in the prior art that these compounds have any pharmaceutical use. They are described by Drago in "Free Radicals in Inorganic Chemistry", Number 36, Advances in Chemistry Series, American Chemical Society, Wash. DC, 1962, pages 143-149 and Drago et al. J. Amer. Chem. Soc. 83, 1819-1822, 1961. These two articles by Drago are incorporated by reference, in their entirety. The references are of a theoretical nature and mention no utility whatsoever. Reilly, U.S. Pat. No. 3,153,094, discloses these compounds on columns 11-13, but does not teach any biological activity.

DESCRIPTION OF THE INVENTION

The present invention provides pharmaceutical compositions comprising: a compound of the following formula

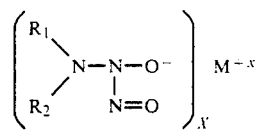

wherein $R_1$ and $R_2$ are independently chosen from straight chain and branched chain alkyl groups of one to twelve carbon atoms or benzyl, with the proviso that no branch occur on the alpha carbon of the alkyl groups, or $R_1$ and $R_2$ together with the nitrogen atom they are bonded to form a pyrrolidino, piperidino, piperazino or morpholino ring, $M^{+x}$ is a pharmaceutically acceptable cation, wherein x is the valence of the cation (its charge); and a pharmaceutically acceptable carrier. By straight chain alkyl is meant the non-branched methyl, ethyl, n-propyl, n-butyl, n-decyl, and etc. groups. By branched chain alkyl is meant groups like 3-methylpentyl, 2-ethylpropyl, and etc. The proviso means that groups like isopropyl or 1-methylbutyl are excluded. The $C_2$ to $C_6$ alkyls are preferred. Of the $R_1R_2N-$ heterocyclic groups, morpholino is preferred. By a pharmaceutically acceptable cation is meant any non-toxic cation; these are well known to one of ordinary skill in the art. The cation should not render the compound unstable or insoluble in water. Generally the cation will be a group 1 or group 2 cation, such as sodium, potassium, magnesium or calcium ions, or $NR_3R_4R_5R_6^+$, wherein $R_3$, $R_4$, $R_5$, and $R_6$ are independently chosen from H, $C_1$-$C_{12}$ alkyl, $C_3$-$C_7$ cycloalkyl or benzyl, more preferably H, $C_1$-$C_4$ alkyl or $C_6$ cycloalkyl. The method of synthesis discussed below first results in the cation being $R_1R_2H_2N^+$, these cations work well. The most preferred cations are $Na^+$, $K^+$, $Ca^{+2}$, and $R_1R_2H_2N^+$.

The compositions are potent anti-hypertensives. They are useful for lowering the blood pressure and treating any cardiovascular disorder in which lowering the blood pressure will have a beneficial effect. The invention provides an effective method of lowering the blood pressure by administering the composition to a mammal.

The methods of synthesis are the same as disclosed by Drago et al., J. Amer. Chem. Soc., 83, 1819-1822, 1961. Generally, the secondary amine ($R_1R_2HN$) is dissolved in anhydrous ether, oxygen is removed from the system, the temperature is lowered to $-78°$ C., and dry NO is bubbled through the ether solution. The reaction can be run at high pressure (100 psi) or at atmospheric pressure. The same product is obtained, but the yields are higher using the high pressure method. The same method is used to make all the compounds, the only difference being the starting secondary amine. Example 1 gives the details of how the diethylamine complex was made.

EXAMPLE 1a

Anhydrous diethylamine (100ml) was dissolved in 100ml of anhydrous diethyl ether and was placed in a three-necked flask. Two of the necks served as inlets for $N_2$ and NO, and the third was an outlet. The flask was flushed with $N_2$ and the mixture cooled to $-78°$ C. using an acetone-dry ice bath. Commercial grade NO was bubbled through 10M NaOH and dried by passing it through a column containing NaOH pellets, and then bubbled for 3 hr through the diethylamine/diethyl ether solution. The mixture was allowed to warm to room temperature overnight (18 hr). The product precipitated from solution. The product was filtered and washed with diethyl ether. Three grams (3% yield) of crude product was obtained. The product was purified by suspending it in diethyl ether, adding sufficient neutralized chloroform dropwise to just dissolve the product, and placing the mixture in the freezer. The resultant crystals were then filtered, washed with diethyl ether and dried by vacuum.

$^1$H NMR(200MHz):δ3.07(q,4H,J=7.2 Hz),2.94(q, 4H,J=7.2Hz),1.27(t, 6H, J=7.2Hz), 0.96(q,6H,J=7.2 Hz).

$^{13}$C NMR(50MHz):δ51.3, 45.2, 13.8, 13.5.

Calculated: C=46.56%, N=27.17%, H=10.75%
Found: C=46.49%, N=26.29, H=11.20%

The above physico-chemical characteristics correspond to the structure:

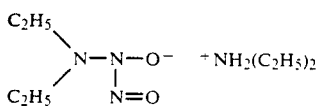

EXAMPLE 1b

In the high pressure method a Parr shaker was used. NO was added to the reservoir which makes it possible to fill the reaction vessel without opening it directly to the NO tank. The mixture of diethylamine (100ml) and diethyl ether (100 ml) was added to the reaction vessel. The reaction vessel was cooled to −78° C. and subjected to several evacuation/nitrogen flush cycles to remove as much of the oxygen as possible. NO was then introduced at a pressure of about 100 psi. The reaction vessel was allowed to slowly warm to room temperature overnight (18 hr), with shaking. The excess NO was flushed off with $N_2$ and the product was filtered and washed with diethyl ether. The crude yield was 5 grams. Purification and analysis were the same as in example 1a.

The other secondary amine-NO complexes are made using the same methods as examples 1a and 1b, the only difference being the identity of the starting secondary amine. The product made in each case has the formula $R_1R_2NN_2O_2R_1R_2H_2N^+$. The synthesis of the salts containing the other cations is done by conventional methods, most particularly by a metathesis reaction, a method well known to one of ordinary skill in the art. (See Drago et al.) To make the sodium salt of the compound produced in example 1, the diethylammonium salt is dissolved in ethyl alcohol and reacted with sodium ethoxide according to the following reaction: $R_1R_2NN_2O_2R_1R_2H_2N^+ + NaOEt \rightarrow EtOH + R_1R_2NH + R_1R_2NN_2O_2Na^+$. The product is precipitated by flooding the reaction mixture with ether and then washed with neutralized chloroform. The other salts can be made by similar metathesis reactions.

PHARMACOLOGICAL PROPERTIES

The effect on the mean arterial blood pressure and heart rate of male Sprague-Dawley rats of the compositions of the invention was measured using a standard technique. A pressure transducer (Bell and Howell, type 4-327-I) was connected to the right carotid artery via a catheter containing heparinized saline. The mean arterial pressure and heart rate were recorded on a Gould (Model 2800) 8-channel recorder. The rats were anesthetized with nembutal at an initial dose of 35 mg/kg body weight and recurrent smaller injections as needed. The compounds were dissolved in a pharmaceutical carrier and injected into the rats via a catheter in the right femoral vein. Table 1 shows the results.

TABLE 1

| Compound | Dose (μmole/kg) | Mean Arterial Pressure (mm Hg) | | | Heart Rate (beats/min) | |
|---|---|---|---|---|---|---|
| | | Initial | Post | Change | Initial | Post |
| $(Et)_2NN_2O_2$ $(Et)_2H_2$ | 3.90 | 102 | 36 | −66 | 480 | 480 |
| SNP | 0.34 | 113 | 56 | −57 | 403 | 454 |
| $NaNO_2$ | 4.00 | 126 | 48 | −78 | 360 | 420 |
| $NaNO_3$ | 42.00 | 117 | 120 | 3 | 420 | 420 |

In Table 1, the pharmaceutical carrier was Abbott's 5% dextrose USP, SNP, $NaNO_2$, and $NaNO_3$ were used as controls. SNP and $NaNO_2$ are known vasodilators, $NaNO_3$ is the oxidative breakdown product of $NaNO_2$ and has little vasodilatory effect. The results show that $(Et)_2NN_2O_2(Et)_2H_2N^+$ is a potent anti-hypertensive, decreasing the blood pressure significantly. The peak value of the blood pressure decrease, shown in Table 1, takes only about 30 sec to 1 min to occur, after injection, and the blood pressure starts to rise again soon after and has totally recovered within 10–15 min.

The compositions of this invention are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency and intracranial hemorrhage. Because of the fast response upon intravenous injection the compositions are particularly advantageous for treating acute disorders such as hypertensive crisis, toxemia of pregnancy and acute congestive heart failure. The preferred method of administration is by injection into the blood system, most preferably by intravenous injection. The chronic disorders can be treated by continuous intravenous infusion. A suitable dosage for intravenous administration is about 0.01 to 10.0 mg/kg per day.

The pharmaceutical compositions of the invention are comprised of the compounds of formula I and a pharmaceutical carrier. The carrier can be any of those conventionally used and is limited only by chemico-physical considerations such as solubility and lack of reactivity with the compound and by the route of administration. For intravenous administration, the carrier will be aqueous and may contain solubilizing agents, buffers, preservatives, antioxidants, chelating agents, and agents to control the tonicity, such as dextrose or sodium chloride. The requirements for effective pharmaceutical carriers for injectable compositions are well known by one of ordinary skill in this art. (See "Pharmaceutics and Pharmacy Practice", J.B. Lippincott Company, Philadelphia, 1982, edited by Banker and Chalmers, pages 238-250, which are incorporated by reference, also see ASHP "Handbook on Injectable Drugs" 4th edition by Trissel, pages 622-630, which lists commercially available intravenous infusion solutions, these pages are incorporated by reference.) The compounds may also be formulated as inclusion complexes, such as, for example, cyclodextrin inclusion complexes; or the compounds may be carried within liposomes. Preferred pharmaceutical carriers for injection are PBS (phosphate buffered saline), 5% dextrose and sterile water. Since the compounds of formula I are subject to being oxidized by oxygen, an antioxidant, such as ascorbate, can be added to the carrier to increase the shelf-life.

What is claimed is:

1. A sterile pharmaceutical composition useful in the treatment of hypertension comprising: an effective amount of a compound of the formula

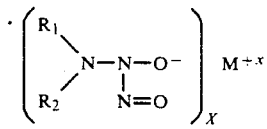

wherein $R_1$ and $R_2$ are independently selected from the group consisting of a straight chain or branched chain $C_1$-$C_{12}$ alkyl group and a benzyl group, with the proviso that no branch occur on the alpha carbon atom, $M^{+x}$ is a pharmaceutically acceptable cation, wherein x is the valence of the cation; and a pharmaceutically acceptable carrier therefor.

2. The composition of claim 1 in a form suitable for injection.

3. The composition of claim 2 wherein $R_1$ and $R_2$ are independently selected from the group consisting of $C_2$-$C_6$ alkyl groups.

4. The composition of claim 3 wherein $M^{+x}$ is selected from the group consisting of group I, group II ions and $NR_3R_4R_5R_6^+$, wherein $R_3$, $R_4$, $R_5$ and $R_6$ are independently selected from the group consisting of H, $C_1$-$C_{12}$ alkyl, $C_3$-$C_7$ cycloalkyl and benzy.

5. The composition of claim 4 wherein $R_1$ and $R_2$ are ethyl.

6. The composition of claim 5 wherein $M^{+x}$ is $Na^+$, $K^+$, $Ca^{+2}$ or $N(C_2H_5)_2H_2^+$.

7. The composition of claim 2, 3, 4, 5 or 6 wherein the pharmaceutically acceptable carrier is selected from the group consisting of sterile water, phosphate buffered saline and aqueous glucose solutions.

8. The pharmaceutical composition of claim 1, wherein said composition is a sterile composition suitable for intravenous injection.

9. The pharmaceutical composition of claim 8, wherein said composition further comprises an antioxidant.

10. A method of treating hypertension in mammals which comprises administering to a mammal, in need thereof, a blood pressure lowering effective amount of a compound of the formula:

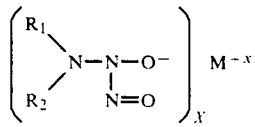

wherein $R_1$ and $R_2$ are independently selected from the group consisting of a straight chain or branched chain $C_1$-$C_{12}$ alkyl group and a benzyl group, with the proviso that no branch occur on the alpha carbon atom; and $M^{+x}$ is a pharmaceutically acceptable cation, wherein x is the valence of the cation.

11. The method of claim 16 wherein $R_1$ and $R_2$ are independently selected from $C_2$-$C_6$ alkyl groups.

12. The method of claim 11 wherein $M^{+x}$ is selected from the group consisting of group I, group II ions and $NR_3R_4R_5R_6^+$, wherein $R_3$, $R_4$, $R_5$ and $R_6$ are independently selected from H, $C_1$-$C_{12}$ alkyl groups, $C_3$-$C_7$ cycloalkyl or benzyl.

13. The method of claim 12 wherein $R_1$ and $R_2$ are ethyl.

14. The method of claim 13 wherein $M^{+x}$ is $NA^+$, $K^+$, $Ca^{+2}$ or $N(C_2H_5)_2H_2^+$.

* * * * *